United States Patent [19]

Shephard et al.

[11] 4,117,147
[45] Sep. 26, 1978

[54] FUNGICIDAL COMPOSITIONS AND PROCESSES

[75] Inventors: Margaret Claire Shephard, Maidenhead; Roland Thomas Victor Fox, Wokingham, both of England

[73] Assignee: Imperial Chemical Industries Limited, London, England

[21] Appl. No.: 831,670

[22] Filed: Sep. 8, 1977

[30] Foreign Application Priority Data

Sep. 22, 1976 [GB] United Kingdom ............... 39267/76

[51] Int. Cl.$^2$ ............................................. A61K 31/40
[52] U.S. Cl. .................................................. 424/274
[58] Field of Search ...................... 424/274; 260/319.1

[56] References Cited

U.S. PATENT DOCUMENTS

| 3,042,685 | 7/1962 | Allais et al. | 260/319.1 |
| 3,291,807 | 12/1966 | Hester | 260/319.1 |

Primary Examiner—Albert T. Meyers
Assistant Examiner—H. S. Seifert
Attorney, Agent, or Firm—Cushman, Darby & Cushman

[57] ABSTRACT

Plant fungal diseases are combatted by treating plants, seeds or soil infested with the disease, or liable to such infestation, with an amount of 6-fluoroindole effective to control the fungus disease.

3 Claims, No Drawings

FUNGICIDAL COMPOSITIONS AND PROCESSES

This invention relates to fungicidal and bactericidal compositions and to processes for combating plant fungi, especially seed and soil borne fungi.

According to the present invention we provide a fungicidal composition comprising 6-fluoroindole. The composition preferably comprises a carrier, the carrier being preferably a solid diluent, or a liquid diluent comprising a surface-active agent.

We further provide, according to the invention, a process for combating plant fungi which process comprises treating plants or seeds, especially cotton and rice, or soil infested with fungi, especially *Rhizoctonia solani*, or liable to such infestation, with 6-fluoroindole, or a composition containing it.

6-Fluoroindole has the structural formula:

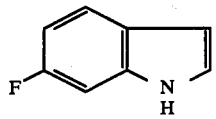

It can be prepared by any of the routes set out and described in the literature, for example, *J. Chem. Sec.*, 1955, 1283–1286.

This compound and compositions containing it are active against various plant, seed and soil-borne fungal and bacterial diseases, but are particularly active against *Rhizoctonia solani* (sore shin on cotton and sheath blight on rice and diseases on other crops). In this latter respect 6-fluoroindole differs from other 5-, 6-, and 7-haloindoles, which are either inactive, or only slightly active, against this particular disease.

The compositions of the invention may be in the form of dusting powders or granules wherein the active ingredient is mixed with a solid diluent or carrier. Suitable diluents or carriers may be, for example kaolin, bentonite, kieselguhr, dolomite, calcium carbonate, talc, powdered magnesia, Fuller's earth, gypsum, Hewitt's earth, diatomaceous earth and China clay.

Compositions for dressing seed, for example, may comprise an agent assisting the adhesion of the composition to the seed, for example a mineral oil.

The composition may also be in the form of dispersible powders or grains comprising, in addition to the active ingredient, a wetting agent to facilitate the dispersion of the powder or grains in liquids. Such powders or grains may include fillers, suspending agents, fertilisers and the like.

The compositions may also be in the form of liquid preparations to be used as dips or sprays which are generally solutions, aqueous dispersions or emulsions containing the active ingredient in the presence of one or more wetting agents, dispersing agents, emulsifying agents or suspending agents.

The aqueous solutions, dispersions or emulsions may be prepared by dissolving the active ingredient in an organic solvent which may contain one or more wetting, dispersing or emulsifying agents and then adding the mixture so obtained to water which may likewise contain one or more wetting, dispersing or emulsifying agents.

The compositions which are to be used in the form of aqueous dispersions or emulsions are generally supplied in the form of a concentrate containing a high proportion of the active ingredient, the said concentrate to be diluted with water before use. These concentrates are often required to withstand storage for prolonged periods and after such storage, to be capable of dilution with water in order to form aqueous preparations which remain homogeneous for a sufficient time to enable them to be applied by conventional spray equipment.

The concentrates may conveniently contain from 10–85% and generally from 25–60% by weight of the active ingredient. When diluted to form aqueous preparations, such preparations may contain varying amounts of the active ingredient depending upon the purpose for which they are to be used, but an aqueous preparation containing between 0.001 and 1.0% by weight of active ingredient may be used. It is to be understood that the fungicidal compositions of this invention may comprise, in addition to 6-fluoroindole one or more other compounds having biological activity.

The invention is illustrated but not limited by the following examples. All constituents are by weight unless otherwise stated.

EXAMPLE 1

An emulsion concentrate was made up by mixing together the ingredients set out below in the proportions stated and stirring the mixture until all the constituents were dissolved.

6-Fluoroindole: 10%
Ethylene dichloride: 40%
Calcium dodecylbenzene-sulphonate: 5%
"Lubrol" L: 10%
"Aromasol" H: 35%

EXAMPLE 2

The active compound was dissolved in a solvent and the resultant liquid was sprayed onto the granules of Fuller's earth. The solvent was then allowed to evaporate to produce a granular composition.

6-Fluoroindole: 5%
Fuller's earth or China clay granules: 95%

The following constitutes an explanation of the compositions or substances represented by the various Trade Marks and Trade Names referred to in the foregoing Examples;

"LUBROL" L — is a condensate of 1 mole of nonyl phenol with 13 molar propartions of ethylene oxide.

"AROMASOL" H — is a solvent mixture of alkylbenzenes.

The chemical referred to in Example 3 below by the common name carboxin, has the structure:

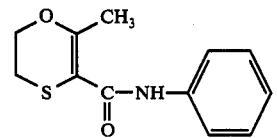

EXAMPLE 3

This Example illustrates the use of the active compound in combating infestation of *Rhizoctonia solani* (sore shin) on cotton. A control experiment was conducted simultaneously with carboxin.

In a test an inoculum of *Rhizoctonia solani* was added to a partially sterilised loam soil with 1% w/w stabilised wheat germ to provide the soil with a 1% w/w content of the inoculum. The loam soil was then allowed to stand for one day so as to be completely colonised by the disease. The compounds were then admixed with the loam soil at a rate of 200 parts per million parts of soil (by weight). After standing for one day to allow the chemical to take effect 7cm square plastic pots were half-filled with untreated, partially sterilised, loam soil and cotton seeds cv "Dettapine" 16 were sown on the surface thereof, whereafter the pots were topped up with the treated loam soil.

The pots were then inspected and assessed 13 days later for disease on the base of the stem and non-emergence of seedlings.

| Chemical | Rate of Application | Percentage amount of disease control |
|---|---|---|
| 6-Fluoroindole | 200 ppm | 92. |
| Carboxin | 200 ppm | 78. |

EXAMPLE 4

This Example illustrates the use of the active compound in combating the disease *Rhizoctonia solani syn. Corticium saskii* (sheath blight of rice). Control experiments were conducted simultaneously with validamycin A* and polyoxin D**.

* See page 510 of the British Crop Protection Council's "Pesticide Manual" — fourth edition.
** See page 418 of the same Manual.

Rice seedlings cv 'Sasanishikii' were grown in 4cm. diameter pots for 12 days and then treated with chemical either as a root drench by adding 10ml. of chemical solution to each pot, or as a spray using the chemical made up in 0.1% 'Tween' 20 as a wetter. The plants were then inoculated the following day by placing 2 plugs 7mm. diameter from a 5 day old culture of *C.sasakii* on a plate of Potato Sucrose Agar on to the surface of the soil.

The plants were kept after inoculation in a humid propagating frame at a temperature between 25°–35° C. The plants were assessed 10 days after inoculation for infection of the leaf bases and sheaths. The results are given below:

| Chemical | Rate of Application | | Percentage Plants found to be healthy | |
|---|---|---|---|---|
| | SPRAY | ROOT DRENCH | SPRAY | ROOT DRENCH |
| 6-Fluoroindole | 250ppm | 100ppm | 100. | 74 |
| Validamydin A | 250ppm | 100ppm | 74. | 74 |
| Polyoxin D | 250ppm | 100ppm | 80. | 70 |
| Untreated | — | — | 32 | 23 |

We claim:

1. A process for combating the fungal disease *Rhizoctonia solani* which comprises treating plants, seeds or soil infested with the disease, or liable to such infestation, with an amount of 6-fluoroindole effective to control said fungus disease.

2. A process according to claim 1 wherein the plants or seeds are cotton or rice.

3. A process according to claim 1, which comprises spraying the foliage of the plants, drenching the soil in the locus of the roots of the plants, or dressing seed before sowing; or any combination thereof.

* * * * *